US012672878B2

(12) United States Patent
Drilling et al.

(10) Patent No.: US 12,672,878 B2
(45) Date of Patent: Jul. 7, 2026

(54) MEDICAL DEVICES FOR TREATING A TARGET SITE AND ASSOCIATED METHOD

(71) Applicant: St. Jude Medical, Cardiology Division, Inc., St. Paul, MN (US)

(72) Inventors: Sarah Ellen Drilling, Minneapolis, MN (US); John C Oslund, Blaine, MN (US); Mathias C Glimsdale, St. Michael, MN (US); Xiaoping Gu, Maplewood, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 640 days.

(21) Appl. No.: 16/994,042

(22) Filed: Aug. 14, 2020

(65) Prior Publication Data

US 2020/0367905 A1      Nov. 26, 2020

Related U.S. Application Data

(63) Continuation of application No. 14/992,516, filed on Jan. 11, 2016, now abandoned, which is a
(Continued)

(51) Int. Cl.
*A61B 17/12* (2006.01)
*A61B 17/00* (2006.01)
(Continued)

(52) U.S. Cl.
CPC .... *A61B 17/12163* (2013.01); *A61B 17/0057* (2013.01); *A61B 17/12022* (2013.01);
(Continued)

(58) Field of Classification Search
CPC .......... A61B 17/0057; A61B 17/12022; A61B 17/12109; A61B 17/12122;
(Continued)

(56) References Cited

U.S. PATENT DOCUMENTS 5,919,224 A      7/1999   Thompson et al.
5,944,738 A      8/1999   Amplatz et al.
(Continued)

FOREIGN PATENT DOCUMENTS

CN           1915188 A      2/2007
JP           10225458 A     8/1998
(Continued)

OTHER PUBLICATIONS

Extended European Search Report issued for EP2244666 on Jun. 26, 2017, 7 pages.
(Continued)

*Primary Examiner* — Katherine M Rodjom
(74) *Attorney, Agent, or Firm* — SLEMAN & LUND LLP

(57) ABSTRACT

Embodiments of the present invention provide devices and methods for treating various target sites, such as vascular abnormalities. For example, a medical device according to one embodiment includes at least one layer of a fabric of braided strands having proximal and distal ends and a central axis extending therebetween. The medical device has an expanded configuration a generally frustroconical shaped portion at each end. The medical device is configured to be constrained to a reduced configuration for delivery through a diagnostic catheter and to at least partially return, when unconstrained, towards the expanded configuration.

19 Claims, 12 Drawing Sheets

FIG. 2A

Related U.S. Application Data continuation of application No. 12/367,104, filed on Feb. 6, 2009, now Pat. No. 9,259,225.

(60) Provisional application No. 61/066,170, filed on Feb. 19, 2008.

(51) Int. Cl.
    *A61M 25/00*          (2006.01)
    *A61M 29/00*          (2006.01)

(52) U.S. Cl.
    CPC .. *A61B 17/12109* (2013.01); *A61B 17/12122* (2013.01); *A61B 17/12172* (2013.01); *A61B 17/12177* (2013.01); *A61M 25/00* (2013.01); *A61M 29/00* (2013.01); *A61B 2017/00575* (2013.01); *A61B 2017/00592* (2013.01); *A61B 2017/00606* (2013.01); *A61B 2017/00849* (2013.01); *A61B 2017/12054* (2013.01); *A61B 2017/12095* (2013.01); *A61M 25/0097* (2013.01)

(58) Field of Classification Search
    CPC ........ A61B 17/12172; A61B 17/12177; A61B 2017/00592; A61B 2017/12054; A61M 29/00

See application file for complete search history.

(56)                    References Cited

U.S. PATENT DOCUMENTS

| | | | |
|---|---|---|---|
| 6,221,086 B1 | 4/2001 | Forber | |
| 6,375,668 B1 * | 4/2002 | Gifford | A61B 17/12022 |
| | | | 606/200 |

| | | | | |
|---|---|---|---|---|
| 2005/0075625 A1 * | 4/2005 | Dao | A61M 25/0074 |
| | | | 977/944 |
| 2005/0131443 A1 | 6/2005 | Abdel-Gawwad | |
| 2005/0228434 A1 | 10/2005 | Amplatz et al. | |
| 2006/0135947 A1 | 6/2006 | Soltesz et al. | |
| 2006/0241690 A1 * | 10/2006 | Amplatz | A61B 17/0057 |
| | | | 606/213 |
| 2007/0043420 A1 | 2/2007 | Lostetter et al. | |
| 2007/0118207 A1 | 5/2007 | Amplatz et al. | |
| 2007/0265656 A1 * | 11/2007 | Amplatz | A61B 17/12122 |
| | | | 606/200 |
| 2007/0292472 A1 * | 12/2007 | Paul | A61B 17/1219 |
| | | | 424/423 |
| 2008/0033475 A1 | 2/2008 | Meng | |
| 2008/0033478 A1 | 2/2008 | Meng | |
| 2008/0200945 A1 | 8/2008 | Amplatz et al. | |
| 2009/0187214 A1 * | 7/2009 | Amplatz | A61B 17/0057 |
| | | | 606/213 |

FOREIGN PATENT DOCUMENTS

| | | | |
|---|---|---|---|
| JP | 11512641 A | 11/1999 | |
| JP | 2002502625 A | 1/2002 | |
| WO | 9601591 A1 | 1/1996 | |
| WO | 9939646 A1 | 8/1999 | |
| WO | WO-2006034153 A2 * | 3/2006 | ....... A61B 17/12022 |
| WO | 2009091425 A1 | 7/2009 | |

OTHER PUBLICATIONS

Chinese Office Action for Application No. 20090106051.X, dated Jun. 8, 2013.

Office Action for Mexican Application No. MX/A/2010/008528; dated May 12, 2013.

* cited by examiner

MEDICAL DEVICES FOR TREATING A TARGET SITE AND ASSOCIATED METHOD

CROSS REFERENCE TO RELATED APPLICATIONS

The present application is a continuation of U.S. patent application Ser. No. 14/992,516, filed Jan. 11, 2016, which is a continuation of U.S. patent application Ser. No. 12/367, 104, filed on Feb. 6, 2009, issued as U.S. Pat. No. 9,259,225, which claims priority to U.S. Provisional Application No. 61/066,170 filed on Feb. 19, 2008, each which is incorporated in its entirety herein by reference.

BACKGROUND OF THE INVENTION

1) Field of the Invention

The present invention relates to medical devices and, in particular, to devices for treating a target site within the body, such as a vascular abnormality.

2) Description of the Related Art

A wide variety of intracardiac prosthetic devices are used in various medical procedures. For example, certain intravascular devices, such as catheters and guide wires, are generally used to deliver fluids or other medical devices to specific locations within the vascular system of a patient, such as a selective coronary artery. Other devices are used in treating specific conditions, such as devices used in removing vascular occlusions or for treating septal defects and the like. For instance, devices have been developed for treating abnormalities, such as an Atrial Septal Defect (ASD), a Ventricular Septal Defect (VSD), a Patent Ductus Arteriosus (PDA), a Patent Foramen Ovale (PFO), as well as conditions that result from previous medical procedures such as Para-Valvular Leaks (PVL) following surgical valve repair or replacement.

However, the ability to deliver these devices to particular areas of the vasculature or for particular patients may be limited by their bulkiness. Previous devices typically require a 6-10 French introducing catheter, which generally makes it difficult to treat children affected with congenital defects with these devices. With respect to a PDA, a smaller, lower profile device potentially allows treatment of pre-mature infants with a PDA. Moreover, some of these devices are used to occlude a patient's vessel or abnormality, such as to stop blood flow through an artery to a tumor or other lesion. Despite the general ability to occlude a vessel or abnormality, reducing the time needed to occlude the vessel or abnormality is desired so that the device may be accurately and effectively positioned and fixated within the vessel.

Furthermore, before delivering these devices, a diagnostic catheter is typically used to inject contrast and then to visualize, by use of angiography, the target site dimensions for proper device selection. Once a device has been selected, the diagnostic catheter is removed from the body and the medical device and delivery catheter are introduced through the vasculature. Thus, conventional medical devices are incapable of being delivered through a diagnostic catheter such that exchanging the diagnostic catheter is required in order to deliver the medical device to the target site.

Accordingly, it would be advantageous to provide a medical device that is deployable through a diagnostic catheter and that may be accurately placed within a target site. In addition, there exists a need for a collapsible medical device for occluding various target sites which provides rapid occlusion following delivery and placement thereof. Moreover, there is also a need for a medical device that may be effectively fixated within a target site.

SUMMARY OF THE INVENTION

Embodiments of the present invention may provide improvements over the prior art by, among other things, providing devices and methods for treating various target sites, such as vascular abnormalities. For example, a medical device according to one embodiment includes at least one layer of a fabric of braided strands having proximal and distal ends and a central axis extending therebetween. The medical device has an expanded configuration including a generally frustroconical shaped portion at each end. The medical device is configured to be constrained to a reduced configuration for delivery through a diagnostic catheter and to at least partially return, when unconstrained, towards the expanded configuration.

According to various aspects of the medical device, the at least one layer of fabric includes braided first and second strands having different first and second diameters. The ends of the braided strands may be secured from unraveling at the proximal and/or distal ends of the medical device. The medical device may include a pair of end clamps securing respective ends of the braided strands and configured for delivery through the diagnostic catheter. One of the end clamps may include a threaded portion. In addition, the fabric may be configured to facilitate thrombosis. The fabric includes a shape memory material such as a shape memory alloy, such as a nickel titanium alloy.

According to additional aspects, the generally frustroconical shaped portions may include first and second ends, with the first ends facing one another and having a larger cross-sectional dimension than that of the second ends, and with the second ends corresponding to the proximal and distal ends of the medical device. Each frustroconical shaped portion may include a planar first end, a cylindrical portion or a curved transition portion extending from the first end, and a conical portion extending from the cylindrical or curved transition portion to the second end. The medical device may further include a central portion coupling the first ends of the frustroconical shaped portions. Furthermore, the central portion may have a cross-sectional dimension substantially less than that of the first ends of the frustroconical shaped portions. The medical device may be configured to be constrained for delivery through a diagnostic catheter having an outer diameter as small as 4 to 5 French or less. The medical device may also be configured to be constrained to a reduced configuration having an outer diameter of less than about 0.040 inches.

According to an additional embodiment of the present invention, a method for treating a target site within the body is provided. The method includes providing a medical device such as that discussed above. The method further includes constraining the medical device from an expanded configuration to a reduced configuration for delivery through a diagnostic catheter and delivering the medical device proximate to the target site. In addition, the method includes deploying the medical device from the diagnostic catheter such that the medical device at least partially returns towards the expanded configuration.

Alternative variations of the method include constraining the medical device to the reduced configuration by axial elongation. Moreover, the method may also include attaching one end of the medical device to a delivery device and advancing the medical device into the diagnostic catheter while attached to the delivery device. The deploying step may include deploying the medical device through a diagnostic catheter having an outer diameter as small as 4 to 5 French or less. The method may further include injecting a contrast medium through the diagnostic catheter before delivering the medical device or after deploying the medical device from the diagnostic catheter.

Another embodiment of the present invention is directed to a delivery system. The delivery system includes a coupler assembly configured to be coupled with a diagnostic catheter and an outer tube coupled to the coupler assembly. The delivery system also includes an elastically compliant member (e.g., a spring) disposed within the outer tube and an inner tube disposed within the outer tube and coupled to the elastically compliant member such that the elastically compliant member is configured to facilitate engagement of the inner tube with the diagnostic catheter when the coupler assembly is coupled to the diagnostic catheter (e.g., via a threaded connection). The inner tube and diagnostic catheter are configured to receive the medical device therein.

According to various aspects of the delivery system, the coupler assembly defines a bore and the inner tube is configured to extend through the bore and be axially displaceable therethrough. The outer tube may have proximal and distal ends, with the elastically compliant member extending from the proximal end and the coupler assembly coupled at the distal end. The inner tube may also have proximal and distal ends, and the elastically compliant member may include first and second opposing ends, wherein the second end of the elastically compliant member and the proximal end of the inner tube are coupled to one another. The elastically compliant member may be configured to urge the distal end of the inner tube into engagement with a diagnostic catheter when the coupler assembly is coupled to the diagnostic catheter. Furthermore, the inner tube may include a tapered distal end configured to extend adjacent to or within a lumen defined by the diagnostic catheter when the diagnostic catheter is coupled to the coupler assembly. The inner tube may also be configured to receive a medical device therein and facilitate delivery of the medical device into the diagnostic catheter. In addition, the coupler assembly, the outer tube, the elastically compliant member, and the inner tube may be disposed coaxially to one another along a common longitudinal axis.

An additional embodiment of the present invention is directed to a method for coupling a delivery system to a diagnostic catheter. The method includes providing a delivery system including a coupler assembly, an outer tube coupled to the coupler assembly, an elastically compliant member disposed within the outer tube, and an inner tube disposed within the outer tube and coupled to the elastically compliant member. The method further includes coupling the diagnostic catheter to the coupler assembly such that the elastically compliant member facilitates engagement of the inner tube with the diagnostic catheter. The coupling step may include biasing the elastically compliant member such that the inner tube is urged into engagement with the diagnostic catheter when the coupler assembly is coupled to the diagnostic catheter. Also, the coupling step may include threadably engaging the coupler assembly to the diagnostic catheter.

Yet another embodiment of the present invention is directed to a kit for use by medical personnel. For example, the kit may include a delivery system, delivery device, and one or more medical devices. A kit could also include a delivery/diagnostic catheter, a guidewire, guidewire torque handle, introducer sheath, and/or any other device used to deliver the medical device.

BRIEF DESCRIPTION OF THE DRAWINGS

The foregoing features and advantages of the invention will become apparent to those skilled in the art from the following detailed description of a preferred embodiment, especially when considered in conjunction with the accompanying drawings in which like numerals in the several views refer to corresponding parts.

DETAILED DESCRIPTION OF THE PREFERRED EMBODIMENTS

Figure 1:
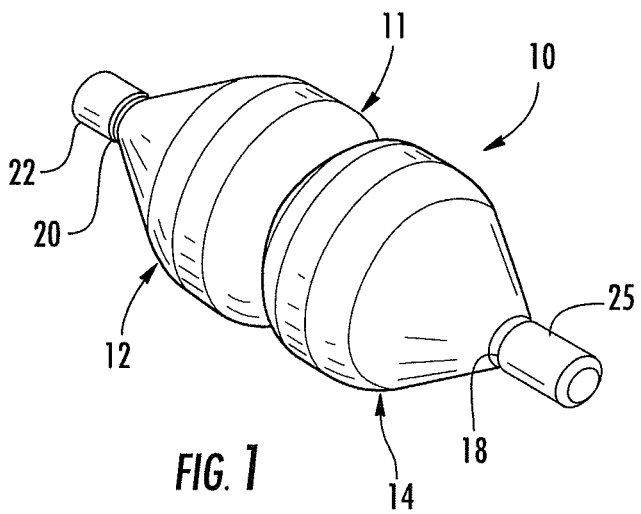
FIG. 1 is a perspective view of an occluder device according to one embodiment of the present invention.

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Embodiments of the present invention provide a medical device for use in treating a target site in a patient's body, such as an aneurysm, a left atrial appendage for patients with left atrial fibrillation, an Arterial Venous Fistula (AVF) or an Arterial Venous Malformation (AVM) or any vessel needed to be occluded to prevent blood flow there through. Other possibilities are treatment of an Atrial Septal Defect (ASD), a Ventricular Septal Defect (VSD), a Patent Foreman Ovale (PFO), or a Patent Ductus Arteriosus (PDA). It is understood that the use of the term "target site" is not meant to be limiting, as the device may be configured to occlude any abnormality, vessel, organ, opening, chamber, channel, hole, cavity, or the like, located anywhere in the body.

As explained in further detail below, embodiments of the present invention are directed to medical devices for treating various target sites. According to one particular aspect, the medical device is dimensioned and configured for delivery through a diagnostic catheter (e.g., as small as 4-5 French and configured to be compatible with about an 0.038 inch diameter guidewire), thereby increasing the efficiency by which the medical device may be deployed within a target site. The medical device may also require less force to be deployed through a delivery system than conventional devices. Moreover, additional embodiments of the present invention are directed to a delivery system for delivering and deploying a medical device at a target site. The delivery system is configured to be engaged with a diagnostic catheter and is adaptable to engage diagnostic catheters having different sizes and configurations. It is understood that the "diagnostic catheter" could be any catheter, tube, or other device capable of being used for diagnosing a target site prior to deploying a medical device (e.g., injecting contrast media) and connected to a delivery system for deploying the medical device therethrough.

According to one embodiment of the present invention for forming a medical device of the invention, the device includes a braided fabric formed of a plurality of wire strands having a predetermined relative orientation with respect to one another. However, it is understood that according to additional embodiments of the present invention, the device may be formed using various techniques. For example, the device could be etched or laser cut from a tube such as to form an interstice geometry, or the device could comprise an occlusion material coupled to a scaffolding structure or a plurality of slices of a tubular member coupled together, such as via gluing. Moreover, it is understood that the device may comprise one or more layers of occluding material such that the device may be a variety of occluding materials capable of at least partially inhibiting blood flow therethrough, facilitating fibrin deposition, formation of organized thrombus, and the formation of scar tissue and epithelization around the device.

Although the term "strand" is discussed herein, "strand" is not meant to be limiting, as it is understood the fabric may comprise one or more wires, cords, fibers, yarns, filaments, cables, threads, or the like, such that such terms may be used interchangeably.

As used herein, "substantially preclude or impede flow" shall mean, functionally, that blood flow may occur for a short time, e.g., about 3-60 minutes through the occlusive material, but that the body's clotting mechanism or protein or other body deposits collecting on the braided wire strands results in occlusion or flow stoppage after this initial time period. For instance, occlusion may be clinically represented by injecting a contrast media into the upstream lumen of the device and if no contrast media flows through the wall of the device after a predetermined period of time as viewed by fluoroscopy, then the position and occlusion of the device is adequate. According to one embodiment, the medical device may be configured to occlude a target site in less than about 10 minutes. Moreover, occlusion of the vascular abnormality could be assessed using various echo modalities.

As used herein the term "proximal" shall mean closest to the operator (less into the body) and "distal" shall mean furthest from the operator (further into the body). In positioning of the medical device from a downstream access point, distal is more upstream and proximal is more downstream.

According to one embodiment, the occlusive material is a metal fabric including a plurality of strands, such as two sets of essentially parallel generally helical strands, with the strands of one set having a "hand", i.e., a direction of rotation, opposite that of the other set. The strands may be braided, interwoven, or otherwise combined to define a generally tubular fabric.

The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. One factor in choosing a suitable material for the wire strands is that the wires retain a suitable amount of the deformation induced by the molding surface (as described below) when subjected to a predetermined heat treatment and elastically return to the molded shape after substantial deformation.

One class of materials which meets these qualifications is so-called shape memory alloys. One particularly preferred shape memory alloy for use in the present method is a NiTi alloy referred to as Nitinol. NiTi alloys are also very elastic—they are said to be "superelastic" or "pseudoelastic". This elasticity may allow the device to return to a preset expanded configuration for deployment following passage in a highly distorted form such as through a delivery catheter. It is also understood that the device may comprise various materials and combinations of materials other than Nitinol that have moderately high elastic properties, such as spring stainless steel, alloys such as Elgiloy®, Hastelloy®, CoCrNi alloys (e.g., trade name Phynox), MP35N®, CoCrMo alloys, or polymeric materials. Polymer fibers may include monofilaments or multifilament yarns ranging from about 10-400 denier. Individual filaments of yarns may range from about 0.25 to 10 denier. Polymers may be composed of PET (Dacron), polyester, polypropylene, polyethylene, HDPE, polyurethane, silicone, PTFE, polyolefins and ePTFE. The metal and plastic fibers may be combined in the same layer, or the tubular layers may be constructed in such a manner that each layer is made from a different material. The polymer layer may be a multifilament braided layer or may be composed of at least one filament or yarn wound about a mandrel with a pitch and diameter similar to other adjacent layers and may be positioned about or inside another adjacent layer or between adjacent layers. Depending on the individual material selected, the wire strand diameter, number of wire strands and pitch may be altered to achieve the desired properties of the device. For example, the strand diameter may be the same for each layer of fabric, different for each layer of fabric, or include strands of different diameters within each layer of fabric (i.e., a hybrid braid). Moreover, other suitable materials include those that are compatible with magnetic resonance imaging (MRI), as some materials may cause heat or torque resulting from performing MRI, and some materials may distort the MRI image. Thus, metallic and/or non-metallic materials that reduce or eliminate these potential problems resulting from using MRI may be employed.

In forming a medical device according to one embodiment of the present invention, an appropriately sized piece of the fabric is cut from the larger piece of fabric which is formed, for example, by braiding wire strands on a mandrel to form a long tubular braid. When cutting the fabric to the desired dimensions, care should be taken to ensure that the fabric will not unravel by clamping the ends of the strands. Clamping may include employing a sleeve, connector, solder, braze, weld, coating, adhesive, clamp, tie or otherwise affixing the ends of the desired length together (e.g., with a biocompatible cementitious organic material).

In addition, a plurality of layers of occlusive material could be separately woven into tubular members, with each tubular member coaxially disposed within another tubular member. For further discussion regarding an exemplary multi-layer device and techniques for fabricating such a device, see U.S. Patent Appl. Publ. No. 2007/0265656 to Amplatz et al., which is hereby incorporated in its entirety by reference.

According to one embodiment, each layer of the device may comprise 36-144 wire strands (e.g., 72 strands) ranging in diameter from about 0.001 to 0.008 in. formed of a shape memory alloy, such as Nitinol, that are braided so as to define fenestrations with an area of about 0.00015 to 0.01 sq. in., which are sufficiently small so as to slow the blood flow through the wall of the device and to facilitate thrombus formation thereon. For a multi-layer device, for instance, the strand diameter of an inner layer may be less than 0.0015 inches or even less than 0.00125 inches, and the strand diameter of an outer layer may be less than 0.002 inches or even less than 0.0015 inches. Each layer may have different strand diameters, for example, the strand diameter of a first inner layer of fabric may be about 0.00125 in., and the strand diameter of a second outer layer may be about 0.0015 in. According to another aspect, the inner and outer layers may have a strand diameter of about 0.0015 in. and 0.002 in., respectively. In another embodiment, a fabric layer may include a hybrid of different strand diameters, such as about 0.00125 and 0.002 in. The inner and outer layers may be braided on a predetermined mandrel size in order to obtain a desired inner diameter of each tubular member, such as about 6 mm diameter mandrel for a fabric layer having a strand diameter of about 0.00125 and 72 strands, and about 8-10 mm diameter mandrel for a fabric layer having a strand diameter of about 0.0015 and 72 strands. The inner and outer braided layers may have pitch angles that are about equal to obtain desirable collapse and expansion characteristics, such as maintaining a uniform overall length. Moreover, the pick-per-inch (PPI) of the braided strands may vary and in one embodiment, is about 85 PPI 0.5 PPI for a outer layer and about 75±0.5 PPI for an inner layer.

Once an appropriately sized piece of the metal fabric is obtained, the fabric is deformed to generally conform to a surface of a molding element. Deforming the fabric will reorient the relative positions of the wire strands of the metal fabric from their initial order to a second, reoriented configuration. The shape of the molding element should be selected to deform the fabric into substantially the shape of the desired medical device when unconstrained. Once the molding element is assembled with the metal fabric generally conforming to a molding surface of that element, the fabric can be subjected to a heat treatment while it remains in contact with that molding surface. After the heat treatment, the fabric is removed from contact with the molding element and will substantially retain its heat set shape in a deformed state.

Those skilled in the art will appreciate that in order to speed up the occlusion of the vessel device, the device may be coated with a suitable thrombogenic agent, filled with a polyester fiber, braided with an increased number of wire strands, or include multiple layers of fabric. The interwoven fiber may attach to a clot to retain the clot firmly within the device as it forms the occlusion.

The device may include a plurality of planes of occlusion. A plane of occlusion may be any surface, whether flat or irregular in shape, that may be oriented generally transverse to the flow of blood so as to facilitate the formation of thrombus. For example, an umbrella shaped plane, even with two layers adhered together on the front and back of a skeleton frame, would be projected as one plane of occlusion. Whereas a device with two umbrella structures, each with their own occlusive material adhered thereto, would project into two planes of occlusion. At least one plane of occlusion may include one or more layers of occlusive material, such as a layer of fabric and/or a layer of polyester fiber, two layers of metal, or two layers of polyester. Thus, by modifying the configuration of the device, the number of planes of occlusion may be modified, and by changing the number of layers of occlusive material, the rate at which the device occludes the vascular abnormality may also be modified.

Referring now to the drawings, a discussion of the embodiments of various medical devices of the present invention will next be presented. For instance, the medical devices or variations there of could be used for treating an Arterial Venous Malformation (AVM), an Atrial Septal Defect (ASD), a Ventricular Septal Defect (VSD), a Patent Ductus Arteriosus (PDA), a Patent Foramen Ovale (PFO), conditions that result from previous medical procedures such as Para-Valvular Leaks (PVL) following surgical valve repair or replacement, and the like.

Figure 2:
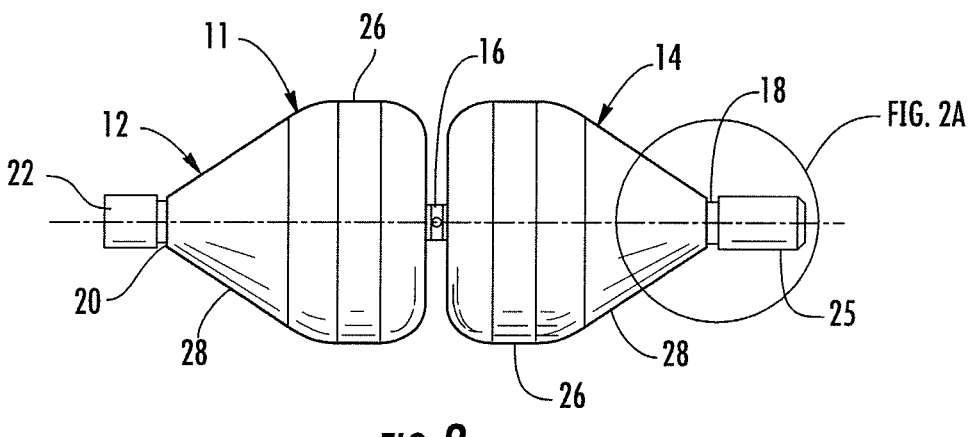
FIG. 2 is a side elevational view of the occluder device shown in FIG. 1.

For example, FIG. 1 illustrates one embodiment of the present invention wherein the medical device 10 is an occluder device. In particular, the medical device 10 includes a tubular member 11 having a pair of end sections 12, 14 and a central portion 16 (see FIG. 2) extending therebetween. The end sections 12, 14 typically have a larger cross-sectional dimension than that of the central portion 16. The end sections 12, 14 may be a variety of shapes configured to conform to a target site. For example, FIGS. 1 and 2 show that the end sections 12, 14 may be generally frustroconical in shape. Namely, each end section 12, 14 may include a generally cylindrical portion 26 and a generally conical portion 28, wherein the cylindrical portions are coupled together by the central portion 16 and the conical portions extend from the cylindrical portions and taper to respective proximal 18 and distal 20 ends of the device 10. Alternatively the cylindrical portion 26 may be replaced by a curved surface transitioning from the planar end to the conical portion. The generally frustroconical shaped end sections 12, 14 are configured to reduce the amount of force needed to deploy the device 10 through a delivery catheter such as a diagnostic catheter, while providing sufficient device retention force after deployment into a target site within the body. According to one aspect, the force required to advance, or deploy, or recapture the device 10 through the delivery catheter is less than 1.5 $lb_f$.

Figure 4:
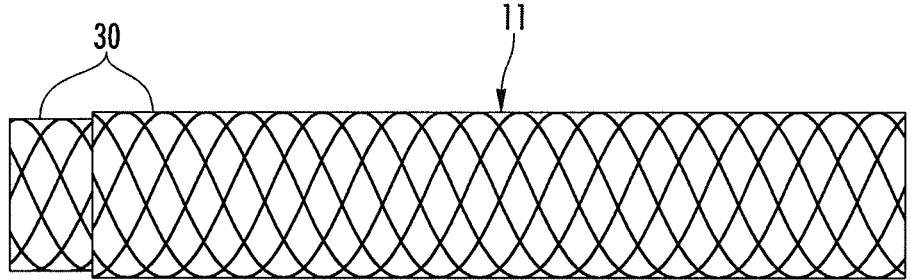
FIG. 4 is a side elevational view of a multi-layer tubular member for forming an occluder device according to one embodiment of the present invention.
Figure 9:
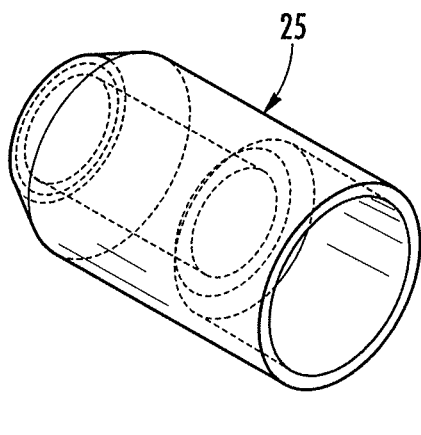
FIG. 9 is a perspective view of an end clamp according to an embodiment of the present invention.
Figure 10:
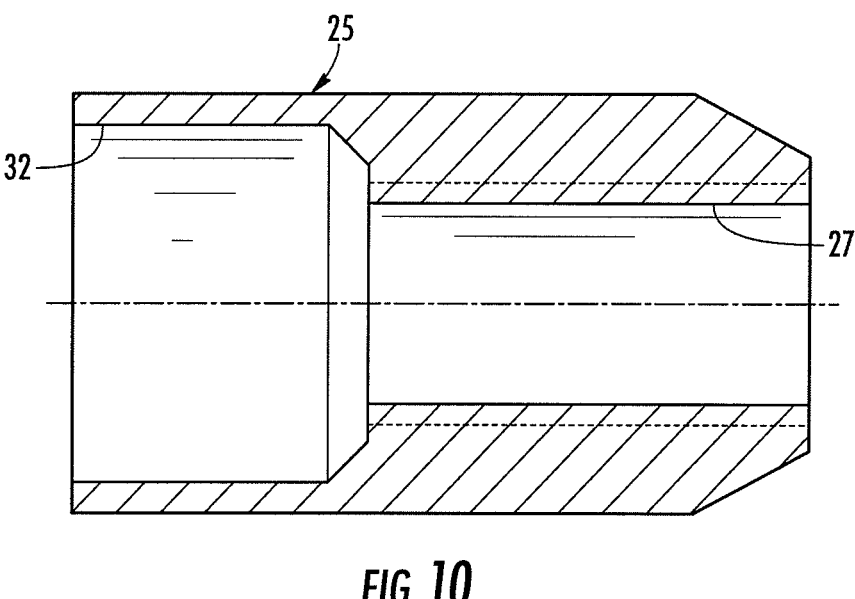
FIG. 10 is a cross-sectional view of the end clamp shown in FIG. 9.
Figure 11:
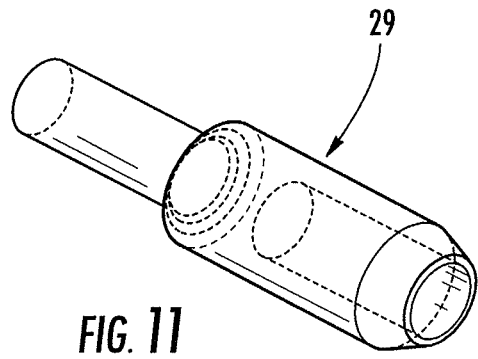
FIG. 11 is a perspective view of an end screw for a delivery device according to one embodiment of the present invention.
Figure 12:
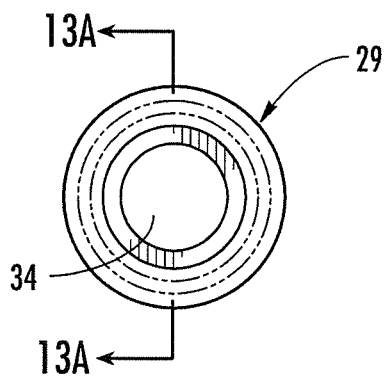
FIG. 12 is an end view of the end screw shown in FIG. 11.
Figure 13:
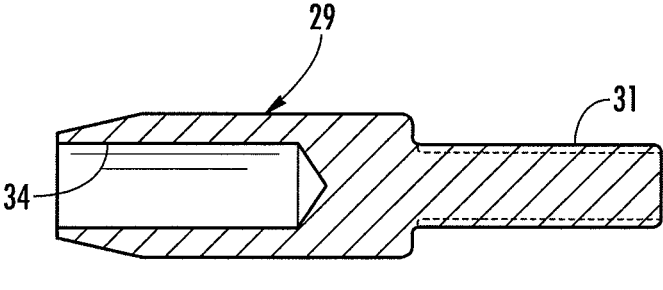
FIG. 13 is a cross-sectional view of the end screw shown in FIG. 11.
Figure 11A:
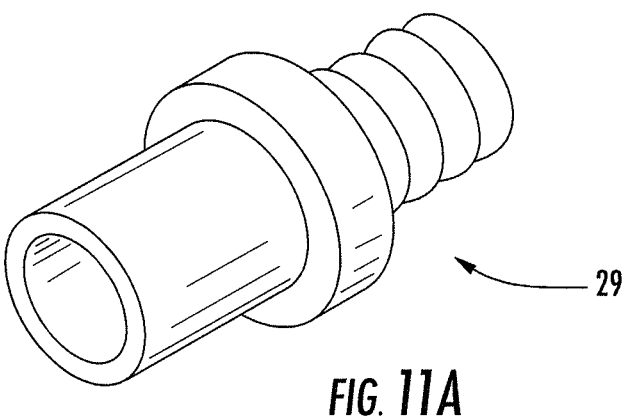
FIG. 11A is a perspective view of an end screw for a delivery device according to another embodiment of the present invention.
Figure 12A:
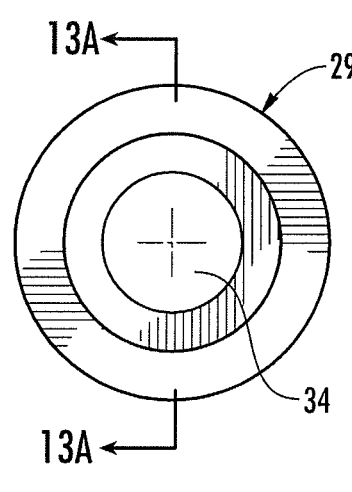
FIG. 12A is an end view of the end screw shown in FIG. 11A.
Figure 13A:
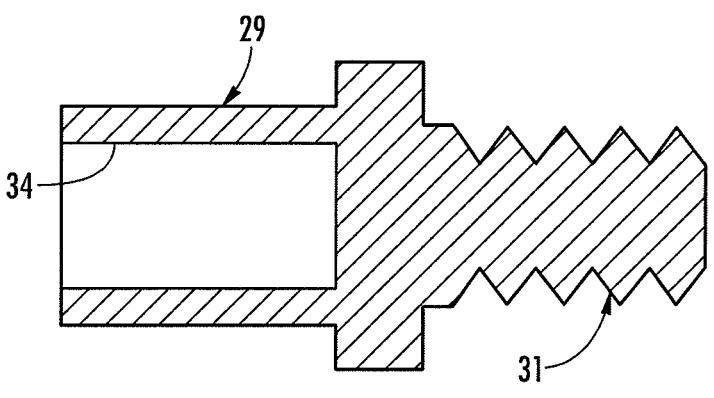
FIG. 13A is a cross-sectional view of the end screw shown in FIG. 11A.
Figure 21:
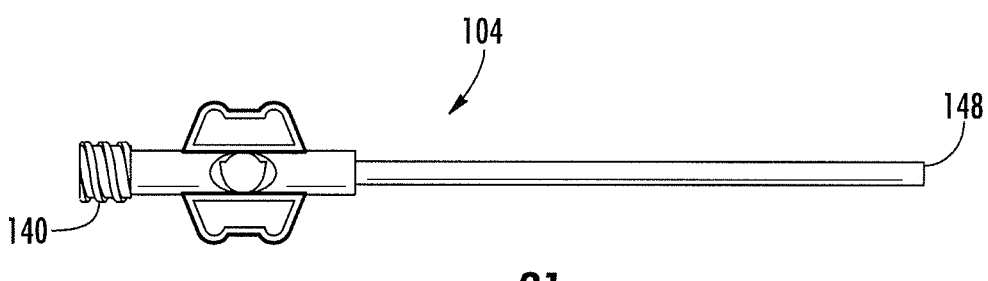
FIG. 21 is a side elevational view of a diagnostic catheter according to one embodiment of the present invention.

The end sections 12, 14 and central portion 16 may be formed from a single tubular member 11. As described above, the tubular member 11 may be formed from one or more layers of braided fabric with each layer including a plurality of strands. For example, FIG. 4 shows a tubular member 11 formed from two layers of braided fabric 30 that may be sized and configured for delivery through a diagnostic catheter 104 (see FIG. 21). The proximal 18 and distal 20 ends of the medical device 10 may be secured within an opening 32 defined within respective end clamps 22, 25. For instance, FIGS. 2, 9, and 10 illustrate that an end clamp 25 having threads 27 for engagement with an end screw 29 (see FIGS. 11-13 and 11A-13A) of a delivery device 38 (see FIGS. 18 and 19) may be used to secure the proximal end 18 of the medical device 10. For example, the terminating ends of the braided strands at the proximal end 18 of the medical device 10 may be secured with a marker band (such as by swaging, clamping, and/or laser welding), and the end clamp may be positioned over the marker band and welded to the marker band. According to one aspect, the clamp 25 at the proximal end 18 may have female threads 27 for engaging an end screw 29 having male threads 31. In addition, FIG. 2 depicts an end clamp 22 or marker band that may be employed to secure the terminating ends of the braided strands at the distal end 20 of the medical device 10, such as by swaging, clamping, or welding. It is understood that either of the clamps 22, 25 shown in FIG. 2 could be used at one or both ends of the medical device 10.

It is further understood that the clamps 22, 25 and end screw 29 may be various sizes and configurations but are capable of being deployed through the delivery system 100 (see FIGS. 14-19). According to one embodiment, the end clamp 22 could be about 0.029 inches or less in outer diameter. In addition, the outer diameter of the end clamp 25 may be less than about 0.037 inches or less, while the outer diameter of the end screw may also be about 0.037 inches or less. The threads 27 of the end clamp 25 and the threads 31 of the end screw 29 may be, for example, 120 to 160 threads per inch. In one embodiment, the end screw having about a 0.037 inch diameter is the largest profile on the device when elongated and thus assures passage through a 4-8 French diagnostic catheter having a lumen larger than the maximum diameter of the collapsed device. A 4-8 French diagnostic catheter has a lumen, depending on the manufacturer, that minimally allows passage of a 0.038 inch diameter guidewire.

Figure 5:
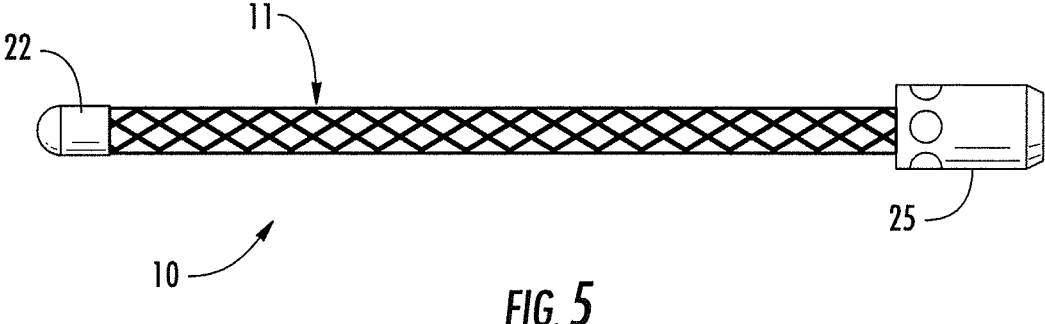
FIG. 5 is a side elevational view of an occluder device in a constrained configuration according to an embodiment of the present invention.

The end sections 12, 14 and central portion 16 may be formed from a single tubular member 11 and heat set in a preset, expanded configuration as described above. For example, FIG. 2 shows the tubular member 11 in a preset, expanded configuration. The tubular member 11 may be formed from a resilient and shape memory material such that the medical device 10 may be constrained from a preset, expanded configuration to a reduced configuration for delivery within a catheter to the target site, as shown in FIG. 5 and explained in further detail below. For instance, the medical device 10 may be elongated by pulling on the proximal 18 and distal 20 ends of the device such that the tubular member 11 is constrained to a reduced diameter. According to one embodiment, the medical device 10, including the tubular member 11 and end clamps 22, 25 are dimensioned and configured for delivery through a diagnostic catheter as small as 4-5 French or even smaller. When deployed, the medical device 10 is configured to return to its preset, expanded configuration, and the delivery device 38 may be unscrewed from the threaded clamp 25 such that the device may be fully deployed.

The medical device 10 may be various sizes and configurations for adapting to a variety of target sites. According to one aspect, the diameter of the central portion 16 may be about 0.5 to 1.5 mm, and the diameter of the cylindrical portion 26 may be about 3 to 14 mm. The length between the proximal 18 and distal 20 ends in a preset, relaxed configuration may be about 9 to 25 mm, while the length of the device in the constrained configuration may be about 9 to 40 mm. Moreover, the length of the central portion 16 may be about 0.015 to 0.025 inches, and the length of each cylindrical portion 26 may be about 2-3 mm. Alternatively each cylindrical portion 26 may be replaced by a convex surface that blends with the conical portion 28 and the end surface on either side of the central portion 16. According to one embodiment, the device 10 is deliverable through a 4-8 French diagnostic catheter (e.g., a diagnostic catheter having a minimum inner lumen diameter of about 0.038 inches).

Figure 3:
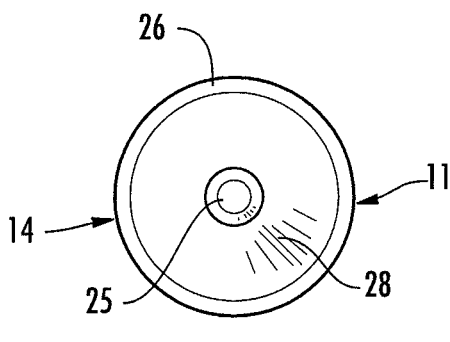
FIG. 3 is an end view of the occluder device shown in FIG. 1.
Figure 6:
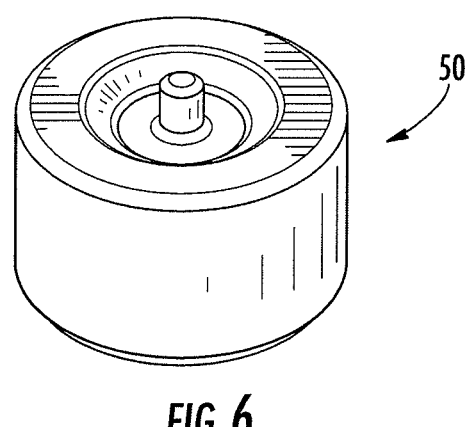
FIG. 6 is a perspective view of an occluder device according to another embodiment of the present invention.
Figure 7:
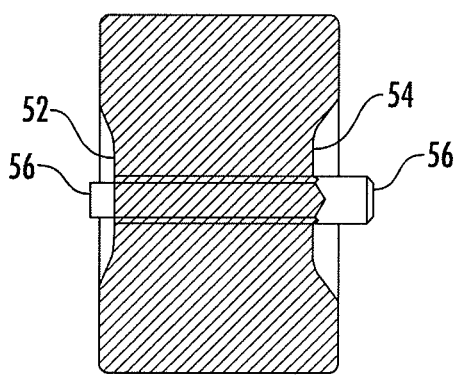
FIG. 7 is a side elevational view of the occluder device shown in FIG. 6.
Figure 8:
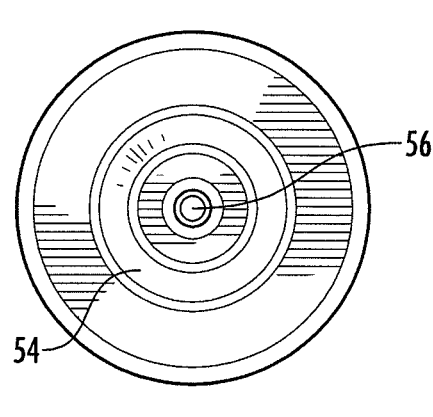
FIG. 8 is an end view of the occluder device shown in FIG. 6.

It is understood that the embodiment of the medical device 10 shown in FIGS. 1-3 is not meant to be limiting, as the medical device may be various sizes and configurations according to additional aspects of the present invention. For instance, the end sections 12, 14 could be other shapes than a frustroconical shape. For instance, the end sections 12, 14 could be a conical, a tear drop, a flat-bottom tear drop shape, or other shape having a convex or otherwise protruding surface that is configured to reduce the amount of force needed to deploy the device through a catheter. According to one alternative embodiment shown in FIGS. 6-8, a medical device 50 has a generally cylindrical shape having concave end surfaces 52, 54. The wire ends at each end surface 52, 54 are secured with a respective end clamp 56, wherein each clamp is at least partially recessed within a respective end surface. At least one end clamp may include threads for connection to a delivery device. According to an exemplary embodiment, the medical device 50 may be about 3-16 mm in outer diameter and about 5-8 mm in length.

Each of the devices discussed above may be used to treat a physiological condition of a patient. Once the appropriate medical device is selected, a delivery system may be employed to deliver and deploy the medical device at the target site. A delivery system 100 according to one embodiment of the present invention is shown in FIGS. 14-19. The delivery system 100 includes a coupler assembly 102 that is adapted to mate with a variety of diagnostic catheters 104 (see FIG. 21), as explained in further detail below. The delivery system 100 includes an outer tube 106 having a distal end 116 coupled to the coupler assembly 102 and an inner tube 108 disposed therein (see FIG. 17). The inner tube 108 is sized and configured to be displaced axially within the outer tube 108. The outer 106 and inner 108 tubes are flexible for conforming to a variety of lumens for delivery and may be clear for enhancing visualization during deployment of the medical device 10. The proximal end 120 of the outer tube 106 is coupled to a housing 122 (see FIG. 15). The housing 122 may be configured to include a pre-slit hemostasis valve 121 and a side port 123 to connect to a stopcock valve 128 for delivering or removing fluid. In addition, the housing 122 includes a bore 131 configured to receive a delivery device 38 or guidewire therethrough, as shown in FIG. 18 and as explained in further detail below. Furthermore, the distal end 114 of the inner tube 108 includes a tapered portion 118 that facilitates insertion within the luer port of a diagnostic catheter 104, bridging the gap between the proximal end of the luer port and the proximal end of the catheter lumen as also explained in additional below.

Figures 14, 15, 16, 17:
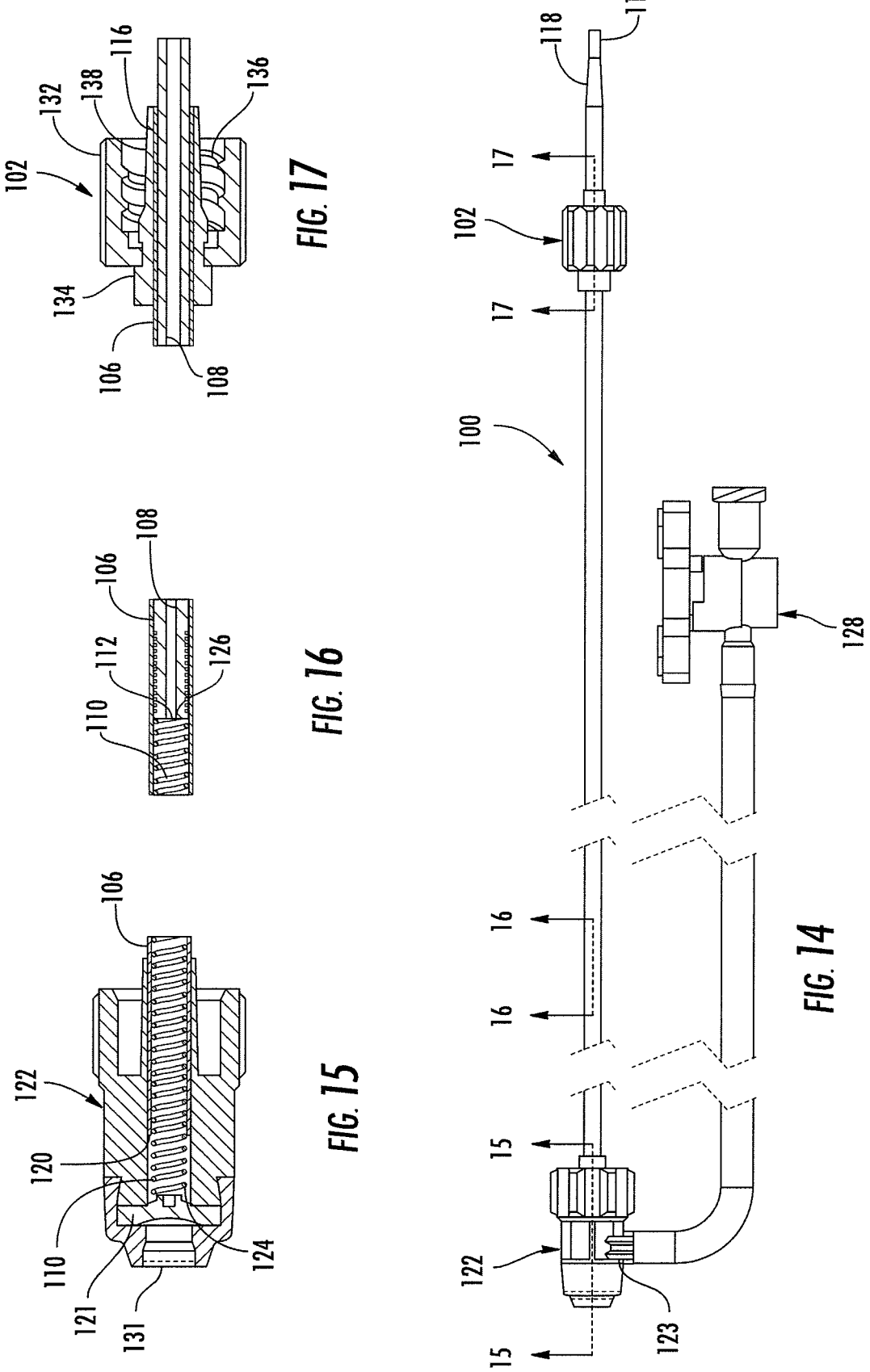
FIG. 14 is a side elevational view of a delivery system for delivering an occluder device according to one embodiment of the present invention.
FIG. 15 is a partial cross-sectional view of the delivery system shown in FIG. 14 illustrating a housing having a spring disposed therein that is coupled to an inner tube.
FIG. 16 is a partial cross-sectional view of the delivery system shown in FIG. 14 showing the outer tube, inner tube, and spring.
FIG. 17 is a partial cross-sectional view of the delivery system shown in FIG. 14 depicting a coupler assembly.
Figures 18, 18A:
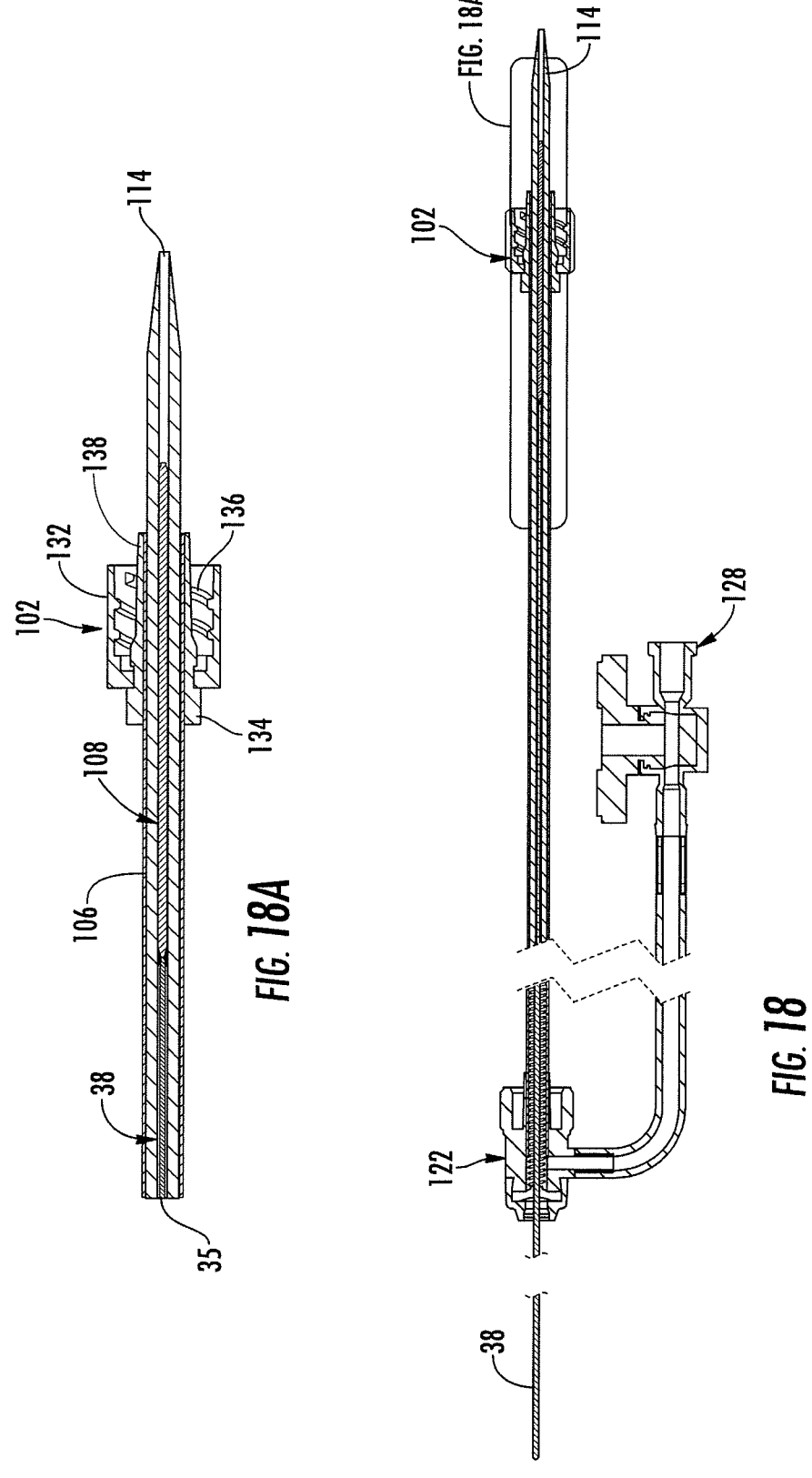
FIG. 18 is a cross-sectional view of the delivery system shown in FIG. 14 having a delivery device extending therethrough.
FIG. 18A is an enlarged view of the coupler assembly having the delivery device extending therethrough.

An elastically compliant member 110 is coupled to the inner tube 108 and disposed within the outer tube 106 (see FIGS. 15 and 16). In particular, a proximal end 124 of the compliant member 110 is partially disposed and affixed within a housing 122, while the distal end 126 is coupled to the proximal end 112 of the inner tube 108. According to one embodiment, the compliant member 110 may be a compression spring that biases the inner tube 108 in a distal direction. Thus, a force applied to the distal end 114 of the inner tube 108 in a proximal direction will move the inner tube proximally, thereby compressing the spring, and when the force is removed, the spring will bias the inner tube back to its relaxed position. The compliant member 110 may be configured to be displaced various distances depending on the amount of adjustment needed to ensure a connection between the coupler assembly 102 and the diagnostic catheter 104. Moreover, the spring force of the compliant member 110 may be any suitable force capable of displacing the inner tube in a distal direction in a relaxed state, while also allowing the inner tube 108 to be displaced proximally for mating with the diagnostic catheter 104.

Figures 19, 19A:
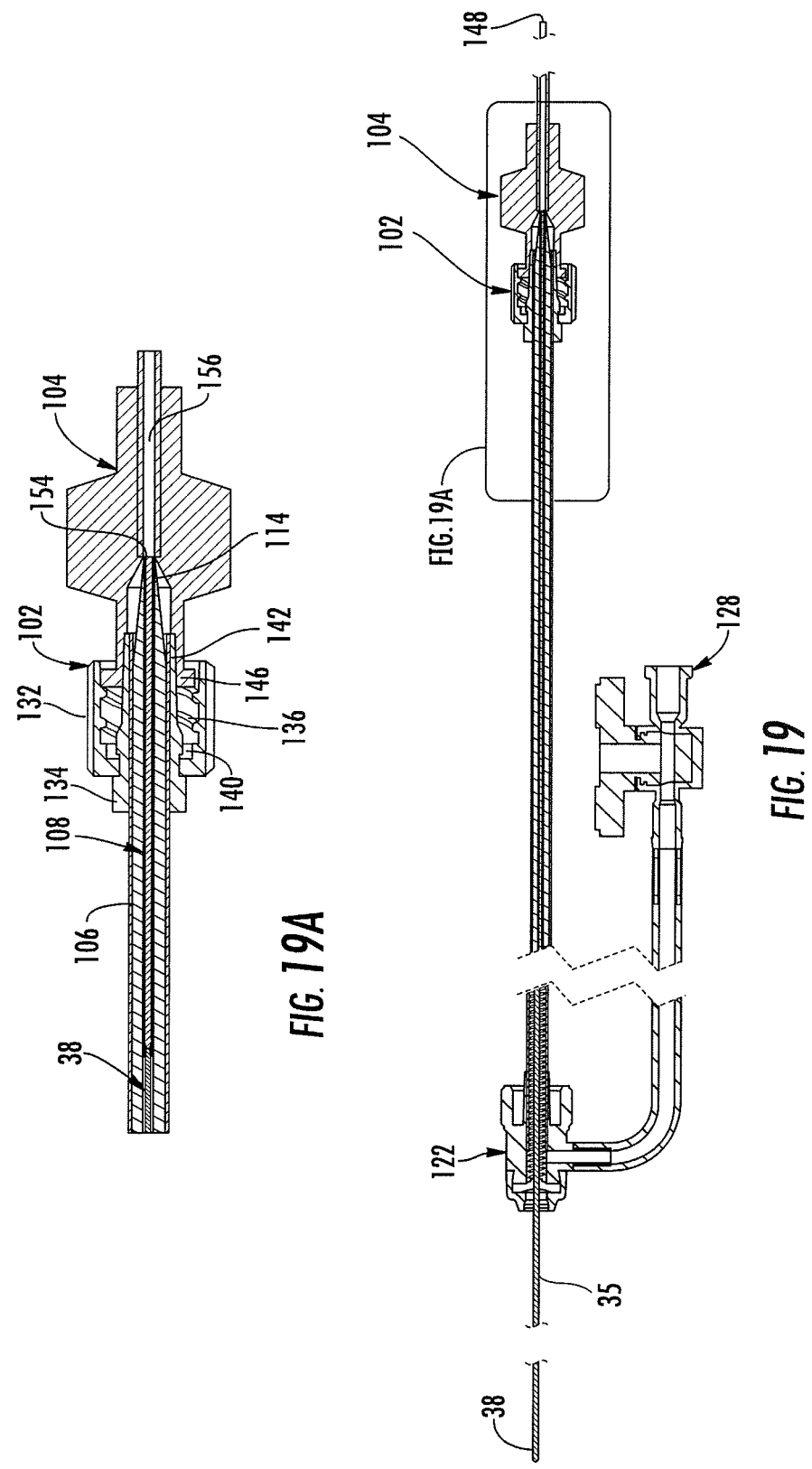
FIG. 19 is a cross-sectional view of the delivery system shown in FIG. 14 coupled to a diagnostic catheter.
FIG. 19A is an enlarged view of the connection between the delivery system and diagnostic catheter shown in FIG. 19.
Figure 20:
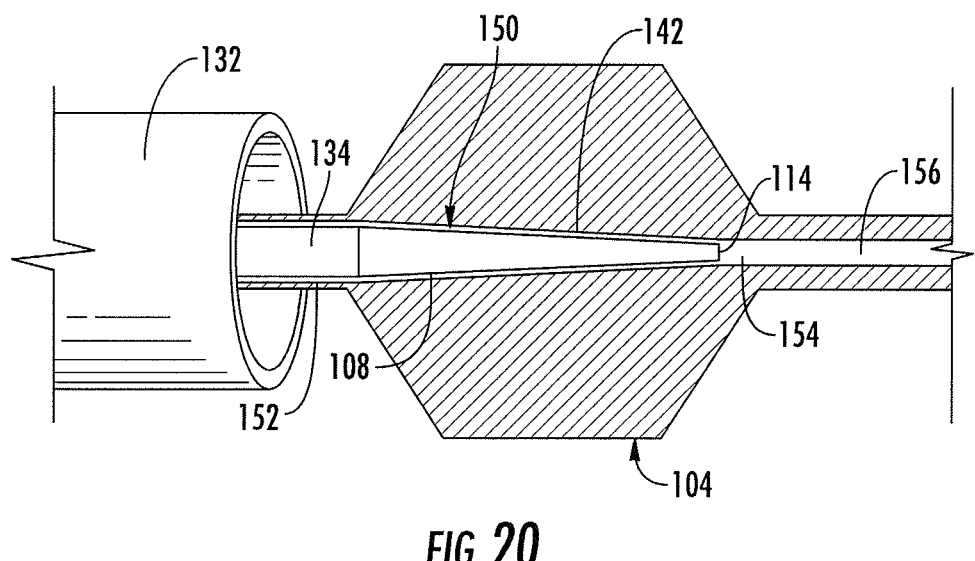
FIG. 20 is another enlarged view of a connection between the delivery system and a diagnostic catheter according to one embodiment of the present invention.

The coupler assembly 102 may include a luer fitting 134 and a coupler 132 (see FIG. 17). The coupler 132 includes a threaded bore 136 that may be configured to mate with a threaded end 140 of the diagnostic catheter 104 (see FIGS. 19A and 21). In addition, the coupler 132 may be configured to rotate about the luer fitting 134 in order to facilitate engagement with the diagnostic catheter 104. The luer fitting 134 is positioned between the outer tube 106 and the coupler 132 and may also be configured to facilitate engagement with the diagnostic catheter 104. Namely, the luer fitting 134 may include a tapered portion 138 that is configured to mate with a corresponding tapered portion 142 of the luer port 150 of the diagnostic catheter 104 as shown in FIGS. 19A and 20.

It is understood that various aspects of the delivery system 100 illustrated and discussed above are not meant to be limiting. For example, the coupler assembly 102 may include any suitable mechanism for facilitating a connection with a diagnostic catheter 104, such as a snap-fit connection. Alternatively, the delivery system 100 may employ alternative means for mating the coupler assembly 102 to a diagnostic catheter 104. For instance, the delivery system 100 may include a compression sleeve to facilitate engagement with the diagnostic catheter 104 such that an elastically compliant member 110 is unnecessary. Furthermore, the delivery system 100 may be various sizes and configurations for delivering a medical device to a particular target site. According to one aspect, the delivery system is about 10-12 inches in length, and the inner tube 108 is configured to be received within the proximal end 152 of the luer port 150 of a 4-8 French diagnostic catheter 104.

Embodiments of the delivery system 100 may facilitate engagement with diagnostic catheters 104 having various sizes and configurations. Thus, the delivery system 100 may be used with diagnostic catheters 104 from different manufacturers that may otherwise typically require a specific delivery system from the manufacturer that is capable of mating with the diagnostic catheter. Specifically, although each manufacturer of diagnostic catheters 104 uses a luer port 150 or connector at the proximal end 152 of the diagnostic catheter, the distance between the proximal end of the luer port and the proximal end 154 of the catheter lumen 156 varies considerably. The spring-loaded inner tube 108 bridges this variable distance, placing the tapered distal end 114 of the inner tube as close as possible to the proximal end 154 of the catheter lumen 156. During delivery of the medical device, the inner tube 108 allows a smooth transition of the medical device from the distal end 114 to the catheter lumen 156. Without this spring-loaded inner lumen, a gap may exist between the inner tube 108 distal end 114 and the proximal end 154 of the diagnostic catheter lumen 156. Since the medical device is designed to self expand, the medical device could expand within the gap to a larger diameter and make it difficult if not impossible to advance the medical device into the catheter lumen 156. By minimizing the length of the gap by use of the tapered, spring-loaded inner tube 108, the gap distance is minimized and the medical device is prevented from self expansion into the gap, thus facilitating device entry into the diagnostic catheter lumen 156. For example, FIGS. 19A and 20 illustrate that the distal end 114 of the inner tube 108 may be positioned just proximal to the proximal end 154 of the diagnostic catheter lumen 156. Depending on the specific diagnostic catheter, the distal end 114 of the inner tube 108 may extend within the lumen 156 of the diagnostic catheter or proximal to the proximal end 154.

The medical device may be inserted into the delivery system 100 by first back loading the delivery device 38 through the distal end 114 of the inner tube 108 until the threaded end screw 29 is near the distal end of the inner tube. The expanded device is threadably attached to the delivery device 35 and while holding the distal end 114 of the inner tube 108, the delivery device is drawn further into the delivery system until the device is drawn into the inner tube completely. The medical device axially elongates to reduce its profile when encountering resistance at the tip of the inner tube 108 distal end 114.

The delivery device 38 can take any suitable shape, such as an elongate flexible wire, cable, or tube for engaging the medical device 10. The delivery device 38 may be coupled within an opening 34 of an end screw 29, wherein the end screw has threads 31 for engaging with a threaded bore 27 formed in the end clamp 25 of the medical device 10. The delivery device 38 may include a cable 35 coupled to the end screw 29 within bore 34, such as by a press fit or welding. The delivery device 38 can be used to urge the medical device 10 through the lumen of the inner tube 108 for deployment in a target site of a patient's body. Moreover, the delivery device 38 may be dimensioned to pass through the lumen of the elastically compliant member 110. When the medical device 10 is deployed out the distal end of the diagnostic catheter 104, the delivery device 38 still will retain it. Once the medical device 10 is properly positioned within the target site, the shaft of the delivery device 38 can be rotated about its axis to unscrew the medical device from the delivery device. The delivery device 38 may comprise a metallic and/or polymeric material. For instance, the delivery device 38 may be a Nitinol material. Alternatively, the delivery device 38 may be a combination of materials, such as a Nitinol wire, a stainless steel ribbon wire wrapped around the Nitinol wire, and a polytetrafluoroethylene (PTFE) coating applied over the assembly. The combination of a small core wire and a ribbon wrapped over the core wire provides a flexible and torqueable delivery device that has a diameter sufficiently small to allow easy passage through the delivery system and diagnostic catheter, but sufficiently large to prevent serpentine flexure of the delivery device within the lumens of the delivery system and diagnostic catheter. The PTFE coating provides improved lubricity to the delivery device. According to one exemplary aspect, the delivery device 38 may be about 50-160 inches in length and about 0.025 to 0.037 inches in outer diameter. In addition, the largest outer diameter of the end screw may be about 0.025 to 0.037 inches. Moreover, the delivery device 38 may have a linear grind at its distal end, which may improve the flexibility of the device and thereby provide improved compatibility with more flexible diagnostic catheters when compared to less flexible sheaths. For example, the length of the linear grind could be about 18-22 cm at the distal end of the delivery device 38.

In one embodiment the medical device 10, the delivery system 100, and diagnostic catheter 104 may accommodate a coaxial guidewire that slideably passes through the device, end clamps 22, 25, and inner tube 108 central lumen, and therefore helps guide the delivery system to the desired location. The guidewire may be delivered independently through the vasculature and across the targeted treatment location or may be extended partially distal to the distal end of the delivery system 100 and advanced with the delivery system while the guidewire is manipulated to guide the medical device 10 to the desired location. In another embodiment, the delivery system 100 is steerable to assist in placement of the delivery system and medical device 10.

By keeping the medical device 10 attached to the delivery device 38, the operator can retract the device for repositioning relative to the target site, if it is determined that the device is not properly positioned. A threaded clamp 25 attached to the medical device 10 allows the operator to control the manner in which the medical device is deployed out the distal end of the diagnostic catheter 104. When the medical device 10 exits the diagnostic catheter 104, it will tend to resiliently return to its preset, expanded shape. When the device 10 returns back into this shape, it may tend to act against the distal end 148 of the diagnostic catheter 104 effectively urging itself forward beyond the end of the catheter. This spring action could conceivably result in improper positioning of the device 10 if the location of the device within a target site is critical, such as where it is being positioned in a shunt between two vessels. Since the threaded clamp 25 can enable the operator to maintain a hold on the device 10 during deployment, the spring action of the device can be controlled by the operator to ensure proper positioning during deployment.

The medical device 10 can be collapsed into its reduced diameter configuration and inserted into the lumen of the inner tube 108. The collapsed configuration of the device 10 may be of any shape suitable for easy passage through the lumen of a catheter and proper deployment out the distal end 148 of the diagnostic catheter 104. For example, the device 10 may have a relatively elongated collapsed configuration wherein the device is stretched along its axis (see e.g., FIG. 5). This collapsed configuration can be achieved simply by stretching the device 10 generally along its axis, e.g., by manually grasping the clamps 22, 25 and pulling them apart, which will tend to collapse the end sections 12, 14 of the device inwardly toward the device's axis. In this regard, these devices are not unlike "Chinese handcuffs", which tend to constrict in diameter under axial tension.

If the device 10 is to be used to permanently occlude a target site in the patient's body, one can simply retract the delivery system 100 and remove it from the patient's body. This will leave the medical device 10 deployed in the patient's vascular system so that it may occlude the target site in the patient's body. In some circumstances, the medical device 10 may be attached to a delivery device 38 in such a manner as to secure the device to the end of the delivery system 100. Before removing the delivery system 100, it may be necessary to detach the medical device 10 from the delivery device 38 before removing the delivery system.

Although the device 10 will tend to resiliently return to its initial expanded configuration, i.e., its shape prior to being collapsed for passage through the delivery system 100, it should be understood that it might not always return entirely to that shape. For example, it may be desirable that the device 10 has a maximum outer diameter in its expanded configuration at least as large as and preferably larger than, the inner diameter of the lumen of the target site in which it is to be deployed. If such a device 10 is deployed in a vessel or abnormal opening having a small lumen, engagement with the lumen will prevent the device from completely returning to its expanded configuration. Nonetheless, the device 10 would be properly deployed because it would engage the inner wall of the lumen to seat the device therein.

The device 10 may be delivered and properly placed using two dimensional ICE, MRI, transesphogeal echocardiography, angiography, and/or Doppler color flow mapping. With the advent of two dimensional Intracardiac Echo (ICE), Magnetic Resonance imaging (MRI), trans-esophageal echocardiography, bi-plane angiography, and Doppler Color Flow Mapping, the approximate anatomy of the target site can be visualized. The device 10 that is employed will be based on the approximate size of the target site to be occluded.

According to one embodiment, the delivery system 100 is connected to a diagnostic catheter 104 as shown in FIGS. 19 and 19A. The hub 146 of the diagnostic catheter 104 may be connected to the coupler assembly 102 by threading the proximal end 140 of the diagnostic catheter within the threaded bore 136 of the luer fitting 134 by rotating the coupler 132. The diagnostic catheter 104 may be employed for delivering contrast media through the diagnostic catheter and to the target site for visualizing the target site prior to deploying the medical device 10. For instance, contrast media could be delivered to the target site via the stopcock 128. Once the target site has been sized and the physician is ready to deploy the medical device 10, the physician may insert the delivery device 38, with the medical device 10 attached thereto, into the delivery system 100 or alternatively the device 38 may be pre-installed at the factory into the delivery system and pre-connected to the delivery device. The physician next connects the delivery system to the diagnostic catheter. Displacement of the delivery device 38 in a distal direction results in moving the medical device through the diagnostic catheter 104 and ultimately out the distal end 144 of the diagnostic catheter. Thus, the physician is not required to first remove the diagnostic catheter 104 prior to deploying the medical device 10 since the medical device, including the end clamps 22, 25, are sized and configured to be delivered through the diagnostic catheter.

The embodiments described above may be employed for treating various target sites, such as PDA, VSD, ASD, PFO, PVL, or any other similar abnormality. The various medical device embodiments described above may have a profile that requires less force to advance, deploy, and recapture the device within the delivery system and diagnostic catheter. The reduced profile of this device may be configured for delivery within a 4-8 French diagnostic catheter. Moreover, because the device is capable of being delivered through a diagnostic catheter, the diagnostic catheter need not be exchanged with the delivery system and the device may be delivered more efficiently. Due to device symmetry, some embodiments are deliverable from either the venous or arterial side of the same defect. Furthermore, embodiments of the delivery system 100 facilitate engagement with diagnostic catheters having various sizes and configurations. Thus, the delivery system 100 may be used with diagnostic catheters from different manufacturers that may otherwise require a specific delivery system for each specific diagnostic catheter.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A medical device comprising:

two layers of a fabric of braided strands, the medical device having proximal and distal ends and a central axis extending therebetween and having an expanded preset configuration comprising a generally frustoconical shaped portion at each end, wherein, in the expanded preset configuration, each frustoconical shaped portion comprises first and second ends and a conical portion disposed therebetween, wherein the first ends are generally planar and face one another and have a larger cross-sectional diameter than the second ends, wherein each frustoconical shaped portion includes a cylindrical portion between the first end and the conical portion, wherein the second ends correspond to the proximal and distal ends of the medical device, wherein the ends of the braided strands are secured from unraveling at the proximal and distal ends of the medical device, wherein the medical device is biased towards the expanded preset configuration such that the medical device is configured to self-expand and at least partially return, when unconstrained, towards the expanded preset configuration, and wherein the frustoconical shaped portions are shaped to reduce an outer profile of the medical device in an elongated, reduced configuration and to reduce (i) an applied axial force required to constrain the medical device in the reduced configuration within a 4 French (Fr) or 5 Fr 0.038-inch guidewire compatible diagnostic catheter for delivery to a target site and (ii) the applied axial force required to deploy the medical device from the diagnostic catheter at the target site, and wherein the medical device further comprises a central portion coupling the first ends of the frustoconical shaped portions, and wherein, in the expanded preset configuration, the central portion has a diameter of between 0.5 mm and 1.5 mm, and the cylindrical portions each have a diameter of between 3 mm and 14 mm.

2. The medical device of claim 1, wherein the fabric of braided strands comprises a shape memory material.

3. The medical device of claim 1, wherein the central portion has a cross-sectional dimension substantially less than that of the first ends of the frustoconical shaped portions.

4. The medical device of claim 1, wherein each frustoconical shaped portion has approximately the same maximum outer diameter when the medical device is in the expanded preset configuration.

5. The medical device of claim 1, wherein the frustoconical shaped portions are spaced axially apart from one another along the central axis so as to define a gap therebetween, the medical device further comprising a central portion coupling the first ends and extending within the gap.

6. The medical device of claim 1, wherein each conical portion is spaced axially from the first end towards the second end along the central axis.

7. The medical device of claim 1, wherein the two layers of the fabric of braided strands each comprise a respective tubular member.

8. The medical device of claim 1, wherein the two layers of the fabric of braided strands are configured to at least partially inhibit the flow of blood between the proximal and distal ends so as to occlude a target site in which the medical device is delivered.

9. The medical device of claim 1, wherein a length of the central portion is significantly less than a length of either generally frustoconical shaped portion in the expanded preset configuration.

10. The medical device of claim 9, wherein the length of the central portion is 0.015 inches-0.025 inches in the expanded preset configuration.

11. The medical device of claim 1, wherein a length of the medical device between the proximal and distal ends of the medical device in the expanded preset configuration is less than 25 mm.

12. The medical device of claim 1, wherein the medical device further comprises a pair of end clamps securing respective ends of the braided strands at the proximal and distal ends of the device, and wherein an outer diameter of one of the end clamps is a maximum outer diameter of the medical device in the reduced configuration.

13. The medical device of claim 1, wherein the medical device further comprises a pair of end clamps securing respective ends of the braided strands at the proximal and distal ends of the device, and wherein a maximum diameter of each frustoconical shaped portion when the medical device is in the expanded preset configuration is at least three times an outer diameter of either of the end clamps.

14. A delivery system comprising:

a 4 Fr or 5 Fr 0.038-inch guidewire compatible diagnostic catheter;

a delivery device having a distal end configured to be inserted within an inner lumen of the diagnostic catheter; and the medical device of claim 1 coupled to a proximal end of the delivery device.

15. A method of treating a target site within a body, the method comprising:

performing a diagnostic procedure implemented using a diagnostic catheter, wherein the diagnostic catheter is a 4 Fr or 5 Fr 0.038-inch guidewire compatible diagnostic catheter;

providing a medical device including two layers of a fabric of braided strands, the medical device having proximal and distal ends and a central axis extending therebetween and having an expanded preset configuration comprising a generally frustoconical shaped portion at each end, wherein, in the expanded preset configuration, each frustoconical shaped portion comprises first and second ends and a conical portion disposed therebetween, wherein the first ends are generally planar and face one another and have a larger cross-sectional diameter than the second ends, wherein each frustoconical shaped portion includes a cylindrical portion between the first end and the conical portion, wherein the second ends correspond to the proximal and distal ends of the medical device, wherein the ends of the braided strands are secured from unraveling at the proximal and distal ends of the medical device, wherein the medical device is biased towards the expanded preset configuration such that the medical device is configured to self-expand and at least partially return, when unconstrained, towards the expanded preset configuration;

constraining the medical device from the expanded preset configuration to a reduced configuration for delivery through the same diagnostic catheter with which the diagnostic procedure was implemented, by applying a reduced axial force associated with the generally frustoconical shaped portions at each end of the medical device;

delivering the medical device through the diagnostic catheter proximate to the target site without withdrawing the diagnostic catheter after the diagnostic procedure; and deploying the medical device from the diagnostic catheter such that the medical device at least partially returns towards the expanded preset configuration, by applying the reduced axial force associated with the generally frustoconical shaped portions at each end of the medical device, wherein the medical device further comprises a central portion coupling the first ends of the frustoconical shaped portions, and wherein, in the expanded preset configuration, the central portion has a diameter of between 0.5 mm and 1.5 mm, and the cylindrical portions each have a diameter of between 3 mm and 14 mm.

16. The method of claim 15, wherein the constraining the medical device to the reduced configuration includes axially elongating the medical device.

17. The method of claim 15, further comprising attaching one end of the medical device to a delivery device and advancing the medical device into the diagnostic catheter while attached to the delivery device.

18. The method of claim 15, wherein the constraining the medical device to the reduced configuration comprises applying the axial force to the medical device, wherein the applied axial force is 1.5 pounds (lb) or less.

19. The method of claim 15, wherein performing a diagnostic procedure comprises delivering contrast media to the target site through the diagnostic catheter.

* * * * *